(12) United States Patent
Müller et al.

(10) Patent No.: US 6,265,613 B1
(45) Date of Patent: Jul. 24, 2001

(54) PHENYLACETIC ACID DERIVATIVES, PROCESS FOR THEIR PREPARATION AND THEIR USE AS PESTICIDES AND FUNGICIDES

(75) Inventors: Bernd Müller, Frankenthal; Hubert Sauter; Herbert Bayer, both of Mannheim; Wassilios Grammenos, Ludwigshafen; Thomas Grote, Schifferstadt; Reinhard Kirstgen, Neustadt; Klaus Oberdorf, Heidelberg; Franz Röhl, Schifferstadt; Norbert Götz, Worms; Michael Rack, Heidelberg; Ruth Müller, Friedelsheim; Gisela Lorenz, Hambach; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/011,893
(22) PCT Filed: Sep. 30, 1996
(86) PCT No.: PCT/EP96/04252
  § 371 Date: Feb. 24, 1998
  § 102(e) Date: Feb. 24, 1998
(87) PCT Pub. No.: WO97/13746
  PCT Pub. Date: Apr. 17, 1997

(30) Foreign Application Priority Data

Oct. 10, 1995 (DE) ............................................... 195 37 749
Oct. 27, 1995 (DE) ............................................... 195 40 092

(51) Int. Cl.[7] .......................... C07C 251/88; A01N 37/50

(52) U.S. Cl. ........................... 564/251; 514/557; 514/561; 514/564; 514/565; 514/576; 514/613; 514/614; 514/631; 514/637; 514/638; 514/639; 564/249; 564/250

(58) Field of Search .......................... 514/9–18, 557–564, 514/565, 561, 576, 613, 614, 631, 637–639; 564/249, 250, 251

(56) References Cited

U.S. PATENT DOCUMENTS 5,453,433  9/1995  Aldous et al. ....................... 514/362

FOREIGN PATENT DOCUMENTS

| 627 411 | * 12/1994 | (EP) . |
| 95/18789 | 7/1995 | (WO) . |
| 95/21153 | 8/1995 | (WO) . |
| 95/21154 | 8/1995 | (WO) . |
| 95/21156 | 8/1995 | (WO) . |

* cited by examiner

Primary Examiner—James O. Wilson
Assistant Examiner—Howard Owens
(74) Attorney, Agent, or Firm—Keil & Weinakuf

(57) ABSTRACT

Phenylacetic acid derivatives of the formula I

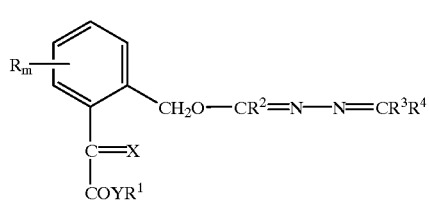

where the substituents and the indexes have the meanings given in the specification, their salts, their preparation and their use.

10 Claims, No Drawings

PHENYLACETIC ACID DERIVATIVES, PROCESS FOR THEIR PREPARATION AND THEIR USE AS PESTICIDES AND FUNGICIDES

BACKGROUND OF THE INVENTION

The present invention relates to phenylacetic acid derivatives of the formula I $$R_m \text{—} \underset{\underset{COYR^1}{\overset{C=X}{|}}}{\text{C}_6H_4}\text{—CH}_2\text{O—CR}^2\text{=N—N=CR}^3R^4 \quad \text{I}$$

where the substituents and the indexes have the following meanings:

X is $NOCH_3$, $CHOCH_3$ and $CHCH_3$;

Y is oxygen or $NR^a$;

$R^a$ is hydrogen or $C_1$–$C_4$-alkyl;

R is cyano, nitro, trifluoromethyl, halogen, $C_1$–$C_4$-alkyl and $C_{1-C4}$-alkoxy;

m is 0, 1 or 2, it being possible for the radicals R to be different if m is 2;

$R^1$ is hydrogen or $C_1$–$C_6$-alkyl;

$R^2$ and $R^3$ independently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3C_6$-cycloalkyl [sic], $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N—$C_3$–$C_6$-cycloalkenyl-N—$C_1$–$C_6$-alkylamino, heterocyclyl, heterocyclyloxy, heterocyclylthio, heterocyclylamino, N-heterocyclyl-N—$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—$D_n$—$R^g$;

A is oxygen, sulfur or nitrogen, the nitrogen having attached to it hydrogen or $C_1$–$C_6$-alkyl;

D is oxygen or $NR^h$;

n is 0 or 1;

$R^b$, $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^4$ is one of the groups mentioned under $R^2$ or a group $CR^d=NOR^e$;

$R^d$ is one of the groups mentioned under $R^2$;

$R^e$ is hydrogen, $C_1$–$C_{10}$-alkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$- alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

$C_3$–$C_6$-cycloalkyl, aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—D—$R^g$;

and to their salts.

The invention furthermore relates to processes for the preparation of these compounds and to compositions comprising them for controlling animal pests and harmful fungi.

The literature discloses phenylacetic acid derivatives for controlling animal pests and harmful fungi (WO-A 95/18, 789, WOP-A 95/21,153, WO-A 95/21,154, WO-A 95/21, 156).

However, it was an object of the present invention to provide compounds with an improved activity.

SUMMARY OF THE INVENTION

We have found that this object is achieved by the phenylacetic acid derivatives I defined at the outset.

We have furthermore found processes for their preparation, compositions comprising them for controlling animal pests and harmful fungi, and their use for this purpose.

DETAILED DESCRIPTION OF THE INVENTION

The compounds I are accessible by various routes by processes known per se from the literature.

In principle, it is immaterial when synthesizing the compounds I whether the group —C(X)—$COYR^1$ or the group —$CH_2OCR^2$=N—N=$CR^3R^4$ is first synthesized.

The synthesis of the group —C(X)—$COYR^1$ is disclosed, for example, in the literature cited at the outset and in EP-A 178 826, EP-A 370 629, EP-A 422 597, EP-A 460 575, EP-A 463 488, EP-A 472 300, EP-A 493 711, EP-A 534 216, EP-A 658 541, EP-A 658 542, EP-A 658 543, WO-A 90/07,493, WO-A 92/13,830, WO-A 92/18,487, EP-A 676 389 and WO-A 95/34,526.

The way in which the —$CH_2OCR^2$=N—N=$CR^3R^4$ lateral chain is synthesized depends essentially on the nature of the substituents $R^2$.

1. In the event that $R^2$ is other than halogen, a procedure is generally followed when synthesizing the group $CH_2OCR^2$=N—N=$CR^3R^4$ in which a benzyl derivative of the formula II is reacted with a carbohydrazide of the formula III.

O=$CR^2$—NH—N=$CR^3R^4$  +

III

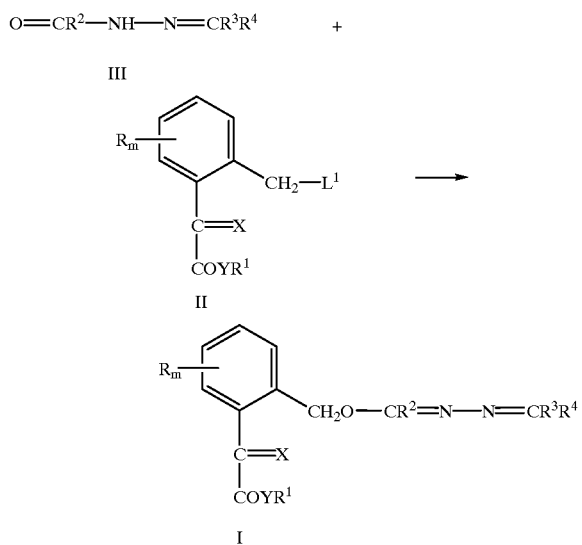

$L^1$ in formula II is a nucleophilically exchangeable leaving group, eg. halogen or sulfonate groups, preferably chlorine, bromine, iodine, mesylate, tosylate or triflate.

The reaction is carried out in the manner known per se in an inert organic solvent in the presence of a base, eg. sodium hydride, potassium hydroxide, potassium carbonate and triethylamine, following the methods described in Houben-Weyl, Vol. E 14b, p. 370 et seq. and Houben-Weyl, Vol. 10/1, p. 1189 et seq.

The carbohydrazide III which is required is obtained by methods known from the literature [eg. Tetrahedron 1987, 4185; Houben-Weyl, Register der Stoffklassen [Register of substance classes] Part A, Vol. 16/2, p. 439 et seq.].

2. Compounds where $R^2$ is a halogen atom are obtained by methods known per se from the corresponding precursors where the radical in question is a hydroxyl group (cf. Houben-Weyl, Vol. E5, p. 631; J. Org. Chem. 36, (1971) 233; J. Org. Chem. 57, (1992) 3245).

3. Compounds where $R^2$ is bonded to the skeleton of the molecule via an O, S or N atom are obtained by methods known per se from the corresponding precursors where the radical in question is a halogen atom (cf. Houben-Weyl, Vo. E5, p. 826 et seq. and 1280 et seq., J. Org. Chem. 36, (1971) 233, J. Org. Chem. 46, (1981) 3623).

4. Some of the compounds where $R^2$ is bonded to the molecule via an oxygen atom are obtained by methods known per se from the corresponding precursors where the radical in question is a hydroxyl group (cf. Houben-Weyl, Vol. E5, p. 826–829, Aust. J. Chem. 27, 1341–9 (1974)).

5. Compounds of the formula I where Y is NRa are obtained from the corresponding compounds Ia in a manner known per se by reacting them with an amine of the formula IV.

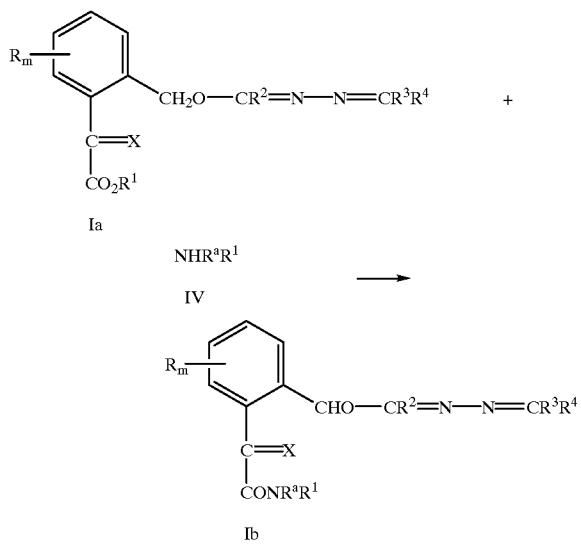

The ester Ia is usually reacted with the amine at from 0° C. to 100 ° C., preferably 15° C. to 70° C., in accordance with [cf. EP-A 579 124].

Useful solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, especially preferably toluene, methanol, tert-butyl methyl ether, dimethylformamide and water. Mixtures of these can also be used.

In general, the starting materials are reacted with each other in equimolar amounts. It may be advantageous for the yield to employ $NHR^aR^1$ in an excess based on Ia.

Those compounds II which are not already known (EP-A 513 580, EP-A 477 631, EP-A 460 575, EP-A 463 488, EP-A 370 692) can be prepared by the methods described in these publications.

Those other starting materials which are required for the preparation of the compounds I and which have not already been described in the literature [cf., for example, Tetrahedron 1987, 4185; Houben-Weyl, Register der Stoffklassen [Register of substance classes] Part A, Vol. 16/2, p. 439 et seq.] can be prepared in accordance with the literature cited.

The reaction mixtures are worked up in the customary manner, for example by mixing with water, separating the phases and, if desired, chromatographic purification of the crude products. Some of the intermediates and end products are obtained in the form of colorless or pale brown viscous oils which are freed, or purified, from volatile components under reduced pressure and at moderately elevated temperature. If the intermediates and end products are obtained as solids, they can also be purified by recrystallization or digestion.

The compounds I can be obtained from the preparation in the form of E/Z isomer mixtures due to their C=C and C=N double bonds and can be separated in the individual compounds in the customary manner, for example by crystallization or chromatography.

If isomer mixtures are obtained from the synthesis, however, a separation is generally not absolutely necessary since in some cases the individual isomers can be converted into each other either upon their formulation for use or upon use (for example under the action of light, acids or bases). Such conversions can also take place after application, for example when plants are treated in the treated plant or in the harmful fungus or animal pest to be controlled.

With a view to the C=X double bond, the E isomers of the compounds I are preferred regarding their activity (configuration based on the $OCH_3$ or $CH_3$ group relative to the $COYR^1$ group).

Regarding the $-CR^2=N-N=CR^3R^4$ double bonds, the cis-isomers of the compounds I are generally preferred regarding their activity (configuration based on the radical $R^2$ relative to the $-N=CR^3R^4$ group or based on the radical $R^3$ relative to the $-N=CR^2$ group).

In the definitions of the compounds I given at the outset, collective terms are used which generally represent the following groups:

halogen: fluorine, chlorine, bromine and iodine;
alkyl: straight-chain or branched alkyl groups having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
alkylamino: an amino group which has attached to it a straight-chain or branched alkyl group having 1 to 6 carbon atoms as mentioned above;
dialkylamino: an amino group which has attached to it two straight-chain or branched alkyl groups which are independent of each other and have in each case 1 to 6 carbon atoms as mentioned above;
alkylcarbonyl: straight-chain or branched alkyl groups which have 1 to 10 carbon atoms and are bonded to the skeleton via a carbonyl group (—CO—);
alkylsulfonyl: straight-chain or branched alkyl groups which have 1 to 6 or 10 carbon atoms and which are bonded to the skeleton via a sulfonyl group (—$SO_2$—);
alkylsulfoxyl: straight-chain or branched alkyl groups which have 1 to 6 carbon atoms and which are bonded to the skeleton via a sulfoxyl group (—S(=O)—);
alkylaminocarbonyl: alkylamino groups which have 1 to 6 carbon atoms as mentioned above and which are bonded to the skeleton via a carbonyl group (—CO—);
dialkylaminocarbonyl: dialkylamino groups which have in each case 1 to 6 carbon atoms per alkyl radical as mentioned above and which are bonded to the skeleton via a carbonyl group (—CO—);
alkylaminothiocarbonyl: alkylamino groups which have 1 to 6 carbon atoms as mentioned above and which are bonded to the skeleton via a thiocarbonyl group (—CS—);
dialkylaminothiocarbonyl: dialkylamino groups which have in each case 1 to 6 carbon atoms per alkyl radical as mentioned above and which are bonded to the skeleton via a thiocarbonyl group (—CS—);

haloalkyl: straight-chain or branched alkyl groups having 1 to 6 carbon atoms, it being possible for some or all of the hydrogen atoms in these groups to be replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups which have 1 to 4 or 6 carbon atoms as mentioned above and which are bonded to the skeleton via an oxygen atom (—O—), eg. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

alkoxycarbonyl: straight-chain or branched alkyl groups which have 1 to 6 carbon atoms and which are bonded to the skeleton via an oxycarbonyl group (—OC(=O)—);

haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

alkylthio: straight-chain or branched alkyl groups which have 1 to 4 or 6 carbon atoms as mentioned above and which are bonded to the skeleton via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, eg. cyclopropyl, cyclobutyl, cyclopentyl and cyclohexyl;

alkenyl: straight-chain or branched alkenyl groups having 2 to 6 or 10 carbon atoms and one double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1- ethyl-1-methyl-2-propenyl, 1-ethyl-2-methyl-1-propenyl and 1-ethyl-2-methyl-2-propenyl;

alkenyloxy: straight-chain or branched alkenyl groups which have 2 to 6 carbon atoms and one double bond in any position and which are bonded to the skeleton via an oxygen atom (—O—);

alkenylthio and alkenylamino: straight-chain or branched alkenyl groups which have 2 to 6 carbon atoms and one double bond in any position and which are bonded to the skeleton via a sulfur atom (alkenylthio) and a nitrogen atom, respectively (alkenylamino).

alkenylcarbonyl: straight-chain or branched alkenyl groups which have 2 to 10 carbon atoms and one double bond in any position and which are bonded to the skeleton via a carbonyl group (—CO—);

alkynyl: straight-chain or branched alkynyl groups having 2 to 10 carbon atoms and one triple bond in any position, eg. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy, alkynylthio and alkynylamino: straight-chain or branched alkynyl groups which have 2 to 6 carbon atoms and one triple bond in any position and which are bonded to the skeleton via an oxygen atom (alkynyloxy), a sulfur atom (alkynylthio) or a nitrogen atom (alkynylamino), respectively.

Alkynylcarbonyl: straight-chain or branched alkynyl groups which have 3 to 10 carbon atoms and one triple bond in any position and which are bonded to the skeleton via a carbonyl group (—CO—).

Cycloalkenyl, cycloalkenyloxy. cycloalkenylthio and cycloalkenylamino: monocyclic alkenyl groups having 3 to 6 carbon ring members which are bonded to the skeleton directly or via an oxygen atom (cycloalkenyloxy), via a sulfur atom (cycloalkenylthio) or via a nitrogen atom (cycloalkenylamino), respectively, eg. cyclopropenyl, cyclobutenyl, cyclopentenyl or cyclohexenyl.

Cycloalkoxy, cycloalkylthio and cycloalkylamino: monocyclic alkenyl groups which have 3 to 6 carbon ring members and which are bonded to the skeleton via an oxygen atom (cycloalkyloxy), via a sulfur atom (cycloalkylthio) or via a nitrogen atom (cycloalkylamino), eg. cyclopropyl, cyclobutyl, cyclopentyl or cyclohexyl;

heterocyclyl, heterocyclyloxy, heterocyclylthio and heterocyclylamino: three- to six-membered, saturated or partially unsaturated mono- or polycyclic heterocycles which contain one to three heteroatoms selected from the group consisting of oxygen, nitrogen and sulfur and which are bonded to the skeleton directly or via an oxygen atom (heterocyclyloxy), via a sulfur atom (heterocyclylthio) or via a nitrogen atom (heterocyclylamino), respectively, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, aryl, aryloxy, arylthio. arylcarbonyl and arylsulfonyl: aromatic mono- or polycyclic hydrocarbon radicals which are bonded to the skeleton directly or via an oxygen atom (—O—); (aryloxy), via a sulfur atom (—S—; arylthio), via a carbonyl group (—CO—; arylcarbonyl) or via a sulfonyl group (—SO$_2$—; arylsulfonyl), respectively, eg. phenyl, naphthyl and phenanthrenyl, or phenyloxy, naphthyloxy and phenanthrenyloxy, respectively, and the corresponding carbonyl and sulfonyl radicals;

arylamino: aromatic mono- or polycyclic hydrocarbon radicals which are bonded to the skeleton via a nitrogen atom.

Hetaryl, hetaryloxy, hetarylthio, hetarylcarbonyl and hetarylsulfonyl: aromatic mono- or polycyclic radicals which, besides carbon ring members, can additionally contain one to four nitrogen atoms or one to three nitrogen atoms and one oxygen or one sulfur atom or one oxygen or one sulfur atom and which are bonded to the skeleton directly or via an oxygen atom (—O—; hetaryloxy) or via a sulfur atom (—S—; hetarylthio), via a carbonyl group (—CO—; hetarylcarbonyl) or via a sulfonyl group (—SO$_2$—; hetarylsulfonyl), respectively, eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl,5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and one sulfur or oxygen atom or one oxygen or one sulfur atom: 5-membered hetaryl ring groups which, besides carbon atoms, can contain one to four nitrogen atoms or one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl containing one to three nitrogen atoms or one nitrogen atom and/or one oxygen or sulfur atom: 5-membered hetaryl ring groups which, besides carbon atoms, can contain one to four nitrogen atoms or one to three nitrogen atoms and one sulfur or oxygen atom or one oxygen or one sulfur atom as ring members and in which two adjacent carbon ring members or one nitrogen and one adjacent carbon ring member can be bridged by a buta-1,3-diene-1,4-diyl group;

5-membered hetaryl bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, can contain one to four nitrogen atoms, or one to three nitrogen atoms, respectively, as ring members and in which two adjacent carbon ring members or one nitrogen and one adjacent carbon ring member can be bridged by a buta-1,3-diene-1,4-diyl group, these rings being bonded to the skeleton via one of the nitrogen ring members;

6-membered hetaryl, containing one to three, or one to four, nitrogen atoms, respectively: 6-membered hetaryl ring groups which, besides carbon atoms, can contain one to three, or one to four, nitrogen atoms, respectively, as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered hetaryl ring groups in which two adjacent carbon ring members can be bridged by a buta-1,3-diene-1,4-diyl group, eg. quinoline, isoquinoline, quinazoline and quinoxaline, and the corresponding oxy, thio, carbonyl or sulfonyl groups.

Hetarylamino: aromatic mono- or polycyclic radicals which, besides carbon ring members, additionally can contain one to four nitrogen atoms or one to three nitorgen atoms and one oxygen or one sulfur atom and which are bonded to the skeleton via a nitrogen atom.

The term "partially or fully halogenated" is intended to express that in the groups which are thus characterized some or all of the hydrogen atoms can be replaced by identical or different halogen atoms as mentioned above.

With a view to their biological action, preferred compounds of the formula I are those where m is 0 or 1, in particular 0.

In the event that m is 1, preferred compounds I are those where R is methyl, fluorine or chlorine.

Especially preferred compounds I are those where X is $NOCH_3$ (formula I.1).

Other preferred compounds I are those where X is $CHCH_3$ (formula I.2).

Equally preferred compounds I are those where X is $CHOCH_3$ (formula I.3).

Besides, especially preferred compounds I are those where $R^1$ is methyl.

Moreover, preferred compounds I are those where Y is oxygen (formula Ia).

Equally preferred compounds I are those where Y is $NR^a$, in particular NH (formula Ib).

Other compounds I which are particularly preferred are those where $R^2$ is hydrogen or $C_1$–$C_4$-alkyl.

Other especially preferred compounds I are those where R2 [sic] is cyclopropyl.

Equally especially preferred compounds I are those where $R^2$ is unsubstituted or substituted aryl or hetaryl.

Besides, especially preferred compounds I are those where $R^2$ is unsubstituted or substituted phenyl.

Moreover, especially preferred compounds I are those where $R^2$ is unsubstituted or substituted cyclopropyl.

Compounds I which are also particularly preferred are those where $R^3$ is $C_1$–$C_4$-alkyl, especially methyl.

Other especially preferred compounds I are those where $R^3$ is unsubstituted or substsituted hetaryl, especially unsubstituted or substituted pyridinyl, isoxazolyl or pyrazolyl.

Equally especially preferred compounds I are those where $R^3$ is unsubstituted or substituted aryl, especially unsubstituted or substituted phenyl.

Besides, especially preferred compounds I are those where $R^3$ is unsubstituted or substituted cycloalkyl, especially unsubstituted or substituted cyclopropyl.

Compounds I which are also particularly preferred are those where $R^4$ is $C_1$–$C_4$-alkyl, especially methyl.

Other especially preferred compounds I are those where $R^4$ is unsubstituted or substituted aryl, especially unsubstituted or substituted phenyl.

Equally especially preferred compounds I are those where $R^4$ is unsubstituted or substituted hetaryl, especially unsubstituted or substituted pyridinyl, isoxazolyl or pyrazolyl.

Besides, especially preferred compounds I are those where $R^4$ is unsubstituted or substituted cycloalkyl, especially unsubstituted or substituted cyclopropyl.

Moreover, especially preferred compounds I are those where $R^4$ is the group $CR^d$=$NOR^e$.

Other especially preferred compounds I are those where $R^d$ is $C_1$–$C_4$-alkyl, especially methyl.

Other especially preferred compounds I are those where $R^d$ is unsubstituted or substituted hetaryl, especially unsubstituted or substituted pyridinyl, isoxazolyl and pyrazolyl.

Other especially preferred compounds I are those where $R^d$ is unsubstituted or substituted aryl, especially unsubstituted or substituted phenyl.

Other especially preferred compounds I are those where $R^d$ is unsubstituted or substituted cycloalkyl, especially unsubstituted or substituted cyclopropyl.

Other especially preferred compounds I are those where $R^e$ is $C_1$–$C_4$-alkyl, especially methyl.

Other especially preferred compounds I are those where $R^e$ is unsubstituted or substituted alkenyl, especially allyl and trans-chloroallyl.

Other especially preferred compounds I are those where $R^e$ is unsubstituted or substituted alkynyl, especially propargyl.

Other especially preferred compounds I are those where $R^e$ is alkoxyalkyl, especially methoxyethyl.

Other especially preferred compounds I are those where $R^e$ is unsubstituted or substituted arylalkyl, especially unsubstituted or substituted benzyl.

Other especially preferred compounds I are those where $R^e$ is unsubstituted or substituted hetaryl or hetarylalkyl.

Particularly preferred with a view to their use are the compounds I which are compiled in the tables which follow. In addition, the groups mentioned in the tables for one substituent are, on their own (independently of the combination in which they are mentioned), an especially preferred embodiment of the substituent in question.

TABLE 1

Compounds of the general formula Ia.1, where $R^2$ is cyclopropyl, $R^3$ is methyl and $R^4$ is $R^x$-substituted phenyl where $R^x$ for each compound corresponds to one line of Table A Ia.1

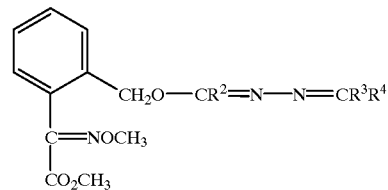

Ia.1

TABLE 2

Compounds of the general formula Ia.2, where $R^2$ is cyclopropyl, $R^3$ is methyl and $R^4$ is $R^x$-substituted phenyl where $R^x$ for each compound corresponds to one line of Table A Ia.2

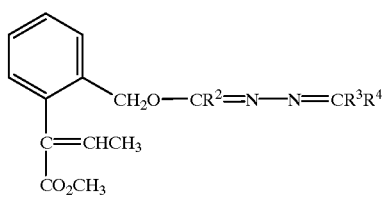

TABLE 3

Compounds of the general formula Ia.3, where $R^2$ is cyclopropyl, $R^3$ is methyl and $R^4$ is $R^x$-substituted phenyl where $R^x$ for each compound corresponds to one line of Table A Ia.3

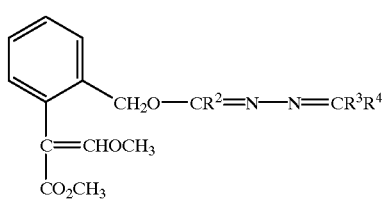

TABLE 4

Compounds of the general formula Ib.1, where $R^2$ is cyclopropyl, $R^3$ is methyl and $R^4$ is $R^x$-substituted phenyl where $R^x$ for each compound corresponds to one line of Table A Ib.1

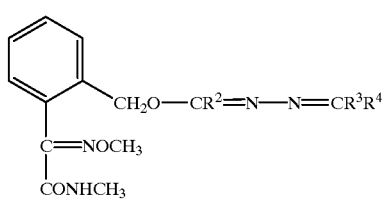

Table 5

Compounds of the general formula Ia.1, where $R^2$, $R^3$ and $R^4$ for each compound corresponds to one line of Table B Table 6

Compounds of the general formula Ia.2, where $R^2$, $R^3$ and $R^4$ for each compound corresponds to one line of Table B Table 7

Compounds of the general formula Ia.3, where $R^2$, $R^3$ and $R^4$ for each compound corresponds to one line of Table B Table 8

Compounds of the general formula Ib.1, where $R^2$, $R^3$ and $R^4$ for each compound corresponds to one line of Table B

TABLE 9

Compounds of the general formula Ia.1.1, where $R^2$ is methyl, $R^d$ is methyl, $R^e$ is methyl and $R^3$ is $R^x$-substituted phenyl where $R^x$ for each compound corresponds to one line of Table A Ia.1.1

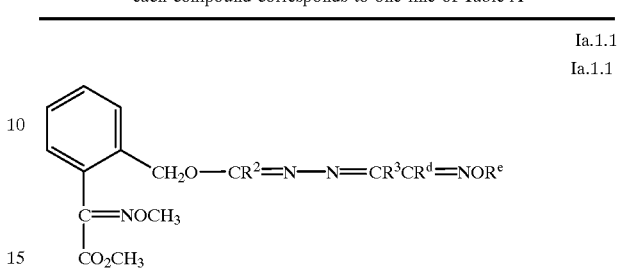

TABLE 10

Compounds of the general formula Ia.1.2, where $R^2$ is methyl, $R^d$ is methyl, $R^e$ is methyl and $R^3$ is $R^x$-substituted phenyl where $R^x$ for each compound corresponds to one line of Table A Ia.1.2

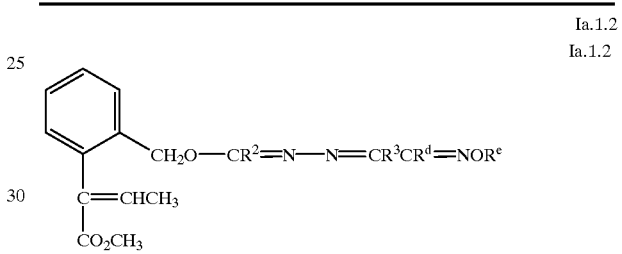

TABLE 11

Compounds of the general formula Ia.1.3, where $R^2$ is methyl, $R^d$ is methyl, $R^e$ is methyl and $R^3$ is $R^x$-substituted phenyl where $R^x$ for each compound corresponds to one line of Table A Ia.1.3

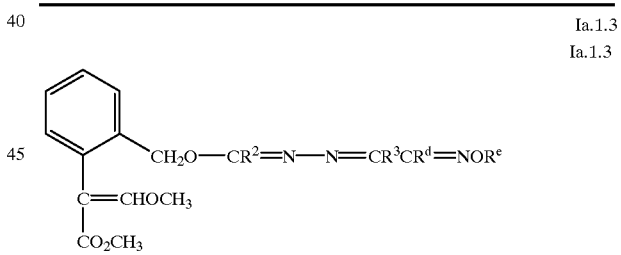

TABLE 12

Compounds of the general formula Ib.1.1, where $R^2$ is methyl, $R^d$ is methyl, $R^e$ is methyl and $R^3$ is $R^x$-substituted phenyl where $R^x$ for each compound corresponds to one line of Table A Ib.1.1

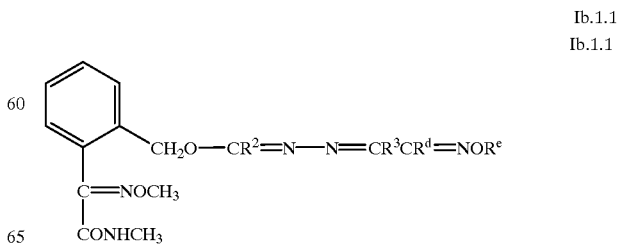

Table 13
Compounds of the general formula Ia.1.1, where $R^2$ is ethyl, $R^d$ is methyl, $R^e$ is methyl and $R^3$ is $R^x$-substituted phenyl where $R^x$ for each compound corresponds to one line of Table A Table 14
Compounds of the general formula Ia.1.2, where $R^2$ is ethyl, $R^d$ is methyl, $R^e$ is methyl and $R^3$ is $R^x$-substituted phenyl where $R^x$ for each compound corresponds to one line of Table A Table 15
Compounds of the general formula Ia.1.3, where $R^2$ is ethyl, $R^d$ is methyl, $R^e$ is methyl and $R^3$ is $R^x$-substituted phenyl where $R^x$ for each compound corresponds to one line of Table A Table 16
Compounds of the general formula Ib1.1, where $R^2$ is ethyl, $R^d$ is methyl, $R^e$ is methyl and $R^3$ is $R^x$-substituted phenyl where $R^x$ for each compound corresponds to one line of Table A Table 17
Compounds of the general formula Ia.1.1, where $R^2$ is cyclopropyl, $R^d$ is methyl, $R^e$ is methyl and $R^3$ is $R^x$-substituted phenyl where $R^x$ for each compound corresponds to one line of Table A Table 18
Compounds of the general formula Ia.1.2, where $R^2$ is cyclopropyl, $R^d$ is methyl, $R^e$ is methyl and $R^3$ is $R^x$-substituted phenyl where $R^x$ for each compound corresponds to one line of Table A Table 19
Compounds of the general formula Ia.1.3, where $R^2$ is cyclopropyl, $R^d$ is methyl, $R^e$ is methyl and $R^3$ is $R^x$-substituted phenyl where $R^x$ for each compound corresponds to one line of Table A Table 20
Compounds of the general formula Ib.1.1, where $R^2$ is cyclopropyl, $R^d$ is methyl, $R^e$ is methyl and $R^3$ is $R^x$-substituted phenyl where $R^x$ for each compound corresponds to one line of Table A Table 21
Compounds of the general formula Ia.1.1, where $R^2$ is methyl, $R^3$ is methyl, $R^e$ is methyl and $R^d$ is $R^x$-substituted phenyl where $R^x$ for each compound corresponds to one line of Table A Table 22
Compounds of the general formula Ia.1.2, where $R^2$ is methyl, $R^3$ is methyl, $R^e$ is methyl and $R^d$ is $R^x$-substituted phenyl where $R^x$ for each compound corresponds to one line of Table A Table 23
Compounds of the general formula Ia.1.3, where $R^2$ is methyl, $R^3$ is methyl, $R^e$ is methyl and $R^d$ is $R^x$-substituted phenyl where $R^x$ for each compound corresponds to one line of Table A Table 24
Compounds of the general formula Ib.1.1, where $R^2$ is methyl, $R^3$ is methyl, $R^e$ is methyl and $R^d$ is $R^x$-substituted phenyl where $R^x$ for each compound corresponds to one line of Table A Table 25
Compounds of the general formula Ia.1.1, where $R^2$ is methyl, $R^3$ is ethyl, $R^e$ is methyl and $R^d$ is $R^x$-substituted phenyl where $R^x$ for each compound corresponds to one line of Table A Table 26
Compounds of the general formula Ia.1.2, where $R^2$ is methyl, $R^3$ is ethyl, $R^e$ is methyl and $R^d$ is $R^x$-substituted phenyl where $R^x$ for each compound corresponds to one line of Table A Table 27
Compounds of the general formula Ia.1.3, where $R^2$ is methyl, $R^3$ is ethyl, $R^e$ is methyl and $R^d$ is $R^x$-substituted phenyl where $R^x$ for each compound corresponds to one line of Table A Table 28
Compounds of the general formula Ib.1.1, where $R^2$ is methyl, $R^3$ is ethyl, $R^e$ is methyl and $R^d$ is $R^x$-substituted phenyl where $R^x$ for each compound corresponds to one line of Table A Table 29
Compounds of the general formula Ia.1.1, where $R^2$ is methyl, $R^3$ is isopropyl, $R^e$ is methyl and $R^d$ is $R^x$-substituted phenyl where $R^x$ for each compound corresponds to one line of Table A Table 30
Compounds of the general formula Ia.1.2, where $R^2$ is methyl, $R^3$ is isopropyl, $R^e$ is methyl and $R^d$ is $R^x$-substituted phenyl where $R^x$ for each compound corresponds to one line of Table A Table 31
Compounds of the general formula Ia.1.3, where $R^2$ is methyl, $R^3$ is isopropyl, $R^e$ is methyl and $R^d$ is $R^x$-substituted phenyl where $R^x$ for each compound corresponds to one line of Table A Table 32
Compounds of the general formula Ib.1.1, where $R^2$ is methyl, $R^3$ is isopropyl, $R^e$ is methyl and $R^d$ is $R^x$-substituted phenyl where $R^x$ for each compound corresponds to one line of Table A Table 33
Compounds of the general formula Ia.1.1, where $R^2$ is methyl, $R^3$ is methyl, $R^e$ is ethyl and $R^d$ is $R^x$-substituted phenyl where $R^x$ for each compound corresponds to one line of Table A Table 34
Compounds of the general formula Ia.1.2, where $R^2$ is methyl, $R^3$ is methyl, $R^e$ is ethyl and $R^d$ is $R^x$-substituted phenyl where $R^x$ for each compound corresponds to one line of Table A Table 35
Compounds of the general formula Ia.1.3, where $R^2$ is methyl, $R^3$ is methyl, $R^e$ is ethyl and $R^d$ is $R^x$-substituted phenyl where $R^x$ for each compound corresponds to one line of Table A Table 36
Compounds of the general formula Ib.1.1, where $R^2$ is methyl, $R^3$ is methyl, $R^e$ is ethyl and $R^d$ is $R^x$-substituted phenyl where $R^x$ for each compound corresponds to one line of Table A Table 37
Compounds of the general formula Ia.1.1, where $R^2$ is methyl, $R^3$ is methyl, $R^e$ is n-propyl and $R^d$ is $R^x$-substituted phenyl where $R^x$ for each compound corresponds to one line of Table A Table 38
Compounds of the general formula Ia.1.2, where $R^2$ is methyl, $R^3$ is methyl, $R^e$ is n-propyl and $R^d$ is $R^x$-substituted phenyl where $R^x$ for each compound corresponds to one line of Table A Table 39
Compounds of the general formula Ia.1.3, where $R^2$ is methyl, $R^3$ is methyl, $R^e$ is n-propyl and $R^d$ is $R^x$-substituted phenyl where $R^x$ for each compound corresponds to one line of Table A Table 40
Compounds of the general formula Ib.1.1, where $R^2$ is methyl, $R^3$ is methyl, $R^e$ is n-propyl and $R^d$ is $R^x$-substituted phenyl where $R^x$ for each compound corresponds to one line of Table A Table 41
Compounds of the general formula Ia.1.1, where $R^2$ is methyl, $R^3$ is methyl, $R^e$ is isopropyl and $R^d$ is $R^x$-substituted phenyl where $R^x$ for each compound corresponds to one line of Table A Table 42
Compounds of the general formula Ia.1.2, where $R^2$ is methyl, $R^3$ is methyl, $R^e$ is isopropyl and $R^d$ is $R^x$-substituted phenyl where $R^x$ for each compound corresponds to one line of Table A Table 43
Compounds of the general formula Ia.1.3, where $R^2$ is methyl, $R^3$ is methyl, $R^e$ is isopropyl and $R^d$ is $R^x$-substituted phenyl where $R^x$ for each compound corresponds to one line of Table A Table 44
Compounds of the general formula Ib.1.1, where $R^2$ is methyl, $R^3$ is methyl, $R^e$ is isopropyl and $R^d$ is $R^x$-substituted phenyl where $R^x$ for each compound corresponds to one line of Table A Table 45
Compounds of the general formula Ia.1.1, where $R^2$ is methyl, $R^3$ is methyl, $R^e$ is tert-butyl and $R^d$ is $R^x$-substituted phenyl where $R^x$ for each compound corresponds to one line of Table A Table 46
Compounds of the general formula Ia.1.2, where $R^2$ is methyl, $R^3$ is methyl, $R^e$ is tert-butyl and $R^d$ is $R^x$-substituted phenyl where $R^x$ for each compound corresponds to one line of Table A Table 47
Compounds of the general formula Ia.1.3, where $R^2$ is methyl, $R^3$ is methyl, $R^e$ is tert-butyl and $R^d$ is $R^x$-substituted phenyl where $R^x$ for each compound corresponds to one line of Table A Table 48
Compounds of the general formula Ib.1.1, where $R^2$ is methyl, $R^3$ is methyl, $R^e$ is tert-butyl and $R^d$ is $R^x$-substituted phenyl where $R^x$ for each compound corresponds to one line of Table A Table 49
Compounds of the general formula Ia.1.1, where $R^2$ is methyl, $R^3$ is methyl, R is benzyl and $R^d$ is $R^x$-substituted phenyl where $R^x$ for each compound corresponds to one line of Table A Table 50
Compounds of the general formula Ia.1.2, where $R^2$ is methyl, $R^3$ is methyl, $R^e$ is benzyl and $R^d$ is $R^x$-substituted phenyl where $R^x$ for each compound corresponds to one line of Table A Table 51
Compounds of the general formula Ia.1.3, where $R^2$ is methyl, $R^3$ is methyl, $R^e$ is benzyl and $R^d$ is $R^x$-substituted phenyl where $R^x$ for each compound corresponds to one line of Table A Table 52
Compounds of the general formula Ib.1.1, where $R^2$ is methyl, $R^3$ is methyl, $R^e$ is benzyl and $R^d$ is $R^x$-substituted phenyl where $R^x$ for each compound corresponds to one line of Table A Table 53
Compounds of the general formula Ia.1.1, where $R^2$ is methyl, $R^3$ is methyl, $R^e$ is propargyl and $R^d$ is $R^x$-substituted phenyl where $R^x$ for each compound corresponds to one line of Table A Table 54
Compounds of the general formula Ia.1.2, where $R^2$ is methyl, $R^3$ is methyl, $R^e$ is propargyl and $R^d$ is $R^x$-substituted phenyl where $R^x$ for each compound corresponds to one line of Table A Table 55
Compounds of the general formula Ia.1.3, where $R^2$ is methyl, $R^3$ is methyl, $R^e$ is propargyl and $R^d$ is $R^x$-substituted phenyl where $R^x$ for each compound corresponds to one line of Table A Table 56
Compounds of the general formula Ib.1.1, where $R^2$ is methyl, $R^3$ is methyl, $R^e$ is propargyl and $R^d$ is $R^x$-substituted phenyl where $R^x$ for each compound corresponds to one line of Table A Table 57
Compounds of the general formula Ia.1.1, where $R^2$ is methyl, $R^3$ is methyl, $R^e$ is bromopropargyl and $R^d$ is $R^x$-substituted phenyl where $R^x$ for each compound corresponds to one line of Table A Table 58
Compounds of the general formula Ia.1.2, where $R^2$ is methyl, R3 is methyl, $R^e$ is bromopropargyl and $R^d$ is $R^x$-substituted phenyl where $R^x$ for each compound corresponds to one line of Table A Table 59
Compounds of the general formula Ia.1.3, where $R^2$ is methyl, $R^3$ is methyl, $R^e$ is bromopropargyl and $R^d$ is $R^x$-substituted phenyl where $R^x$ for each compound corresponds to one line of Table A Table 60
Compounds of the general formula Ib.1.1, where $R^2$ is methyl, $R^3$ is methyl, $R^e$ is bromopropargyl and $R^d$ is $R^x$-substituted phenyl where $R^x$ for each compound corresponds to one line of Table A Table 61
Compounds of the general formula Ia.1.1, where $R^2$ is methyl, $R^3$ is methyl, $R^e$ is iodopropargyl and $R^d$ is $R^x$-substituted phenyl where $R^x$ for each compound corresponds to one line of Table A Table 62
Compounds of the general formula Ia.1.2, where $R^2$ is methyl, $R^3$ is methyl, $R^e$ is iodopropargyl and $R^d$ is $R^x$-substituted phenyl where $R^x$ for each compound corresponds to one line of Table A Table 63
Compounds of the general formula Ia.1.3, where $R^2$ is methyl, $R^3$ is methyl, $R^e$ is iodopropargyl and $R^d$ is $R^x$-substituted phenyl where $R^x$ for each compound corresponds to one line of Table A Table 64
Compounds of the general formula Ib.1.1, where $R^2$ is methyl, $R^3$ is methyl, $R^e$ is iodopropargyl and $R^d$ is $R^x$-substituted phenyl where $R^x$ for each compound corresponds to one line of Table A Table 65
Compounds of the general formula Ia.1.1, where $R^2$ is methyl, $R^3$ is methyl, $R^e$ is allyl and $R^d$ is $R^x$-substituted phenyl where $R^x$ for each compound corresponds to one line of Table A Table 66
Compounds of the general formula Ia.1.2, where $R^2$ is methyl, $R^3$ is methyl, $R^e$ is allyl and $R^d$ is $R^x$-substituted phenyl where $R^x$ for each compound corresponds to one line of Table A Table 67
Compounds of the general formula Ia.1.3, where $R^2$ is methyl, $R^3$ is methyl, $R^e$ is allyl and $R^d$ is $R^x$-substituted phenyl where $R^x$ for each compound corresponds to one line of Table A Table 68
Compounds of the general formula Ib.1.1, where $R^2$ is methyl, $R^3$ is methyl, $R^e$ is allyl and $R^d$ is $R^x$-substituted phenyl where $R^x$ for each compound corresponds to one line of Table A Table 69
Compounds of the general formula Ia.1.1, where $R^2$ is methyl, $R^3$ is methyl, $R^e$ is trans-chloroallyl and $R^d$ is $R^x$-substituted phenyl where $R^x$ for each compound corresponds to one line of Table A Table 70
Compounds of the general formula Ia.1.2, where $R^2$ is methyl, $R^3$ is methyl, $R^e$ is trans-chloroallyl and $R^d$ is $R^x$-substituted phenyl where $R^x$ for each compound corresponds to one line of Table A Table 71
Compounds of the general formula Ia.1.3, where $R^2$ is methyl, $R^3$ is methyl, $R^e$ is trans-chloroallyl and $R^d$ is $R^x$-substituted phenyl where $R^x$ for each compound corresponds to one line of Table A Table 72
Compounds of the general formula Ib.1.1, where $R^2$ is methyl, $R^3$ is methyl, $R^e$ is trans-chloroallyl and $R^d$ is $R^x$-substituted phenyl where $R^x$ for each compound corresponds to one line of Table A Table 73
Compounds of the general formula Ia.1.1, where $R^2$ is methyl, $R^3$ is methyl, $R^e$ is methoxyethyl and $R^d$ is $R^x$-substituted phenyl where $R^x$ for each compound corresponds to one line of Table A Table 74
Compounds of the general formula Ia.1.2, where $R^2$ is methyl, $R^3$ is methyl, $R^e$ is methoxyethyl and $R^d$ is $R^x$-substituted phenyl where $R^x$ for each compound corresponds to one line of Table A Table 75
Compounds of the general formula Ia.1.3, where $R^2$ is methyl, $R^3$ is methyl, $R^e$ is methoxyethyl and $R^d$ is $R^x$-substituted phenyl where $R^x$ for each compound corresponds to one line of Table A Table 76
Compounds of the general formula Ib.1.1, where $R^2$ is methyl, $R^3$ is methyl, $R^e$ is methoxyethyl and $R^d$ is $R^x$-substituted phenyl where $R^x$ for each compound corresponds to one line of Table A Table 77
Compounds of the general formula Ia.1.1, where $R^2$ is methyl, $R^3$ is methyl and $R^4$ is $R^x$-substituted phenyl where $R^x$ for each compound corresponds to one line of Table A Table 78
Compounds of the general formula Ia.2, where $R^2$ is methyl, $R^3$ is methyl and $R^4$ is $R^x$-substituted phenyl where $R^x$ for each compound corresponds to one line of Table A Table 79
Compounds of the general formula Ia.3, where $R^2$ is methyl, $R^3$ is methyl and $R^4$ is $R^x$-substituted phenyl where $R^x$ for each compound corresponds to one line of Table A Table 80
Compounds of the general formula Ib.1.1, where $R^2$ is methyl, $R^3$ is methyl and $R^4$ is $R^x$-substituted phenyl where $R^x$ for each compound corresponds to one line of Table A Table 81
Compounds of the general formula Ia.1.1, where $R^2$, $R^3$, $R^d$ and $R^e$ for each compound correspond to one line of Table C Table 82
Compounds of the general formula Ia.1.2, where $R^2$, $R^3$, $R^d$ and $R^e$ for each compound correspond to one line of Table C Table 83
Compounds of the general formula Ia.1.3, where $R^2$, $R^3$, $R^d$ and $R^e$ for each compound correspond to one line of Table C Table 84
Compounds of the general formula Ib.1.1, where $R^2$, $R^3$, $R^d$ and $R^e$ for each compound correspond to one line of Table C.

Table 85
Compounds of the general formula Ia.1, where $R^2$ is ethyl, $R^3$ is methyl and $R^4$ is $R^x$-substituted phenyl where $R^x$ for each compound corresponds to one line of Table A Table 86
Compounds of the general formula Ia.2, where $R^2$ is ethyl, $R^3$ is methyl and $R^4$ is $R^x$-substituted phenyl where $R^x$ for each compound corresponds to one line of Table A.

Table 87
Compounds of the general formula Ia.3, where $R^2$ is ethyl, $R^3$ is methyl and $R^4$ is $R^x$-substituted phenyl where $R^x$ for each compound corresponds to one line of Table A.

Table 88
Compounds of the general formula Ib.1.1 where $R^2$ is ethyl, $R^3$ is methyl and $R^4$ is $R^x$-substituted phenyl where $R^x$ for each compound corresponds to one line of Table A.

TABLE A

| No. | $R^x$ |
|---|---|
| 1. | H |
| 2. | 2-F |
| 3. | 3-F |
| 4. | 4-F |
| 5. | 2,4-$F_2$ |
| 6. | 2,4,6-$F_3$ |
| 7. | 2,3,4,5,6-$F_5$ |
| 8. | 2,3-$F_2$ |
| 9. | 2-Cl |
| 10. | 3-Cl |
| 11. | 4-Cl |
| 12. | 2,3-$Cl_2$ |
| 13. | 2,4-$Cl_2$ |
| 14. | 2,5-$Cl_2$ |
| 15. | 2,6-$Cl_2$ |
| 16. | 3,4-$Cl_2$ |
| 17. | 3,5-$Cl_2$ |
| 18. | 2,3,4-$CL_3$ |
| 19. | 2,3,5-$CL_3$ |
| 20. | 2,3,6-$CL_3$ |
| 21. | 2,4,5-$CL_3$ |
| 22. | 2,4,6-$CL_3$ |
| 23. | 3,4,5-$CL_3$ |
| 24. | 2,3,4,6-$CL_4$ |
| 25. | 2,3,5,6-$CL_4$ |
| 26. | 2,3,4,5,6-$Cl_5$ |
| 27. | 2-Br |
| 28. | 3-Br |
| 29. | 4-Br |
| 30. | 2,4-$Br_2$ |
| 31. | 2,5-$Br_2$ |
| 32. | 2,6-$Br_2$ |
| 33. | 2,4,6-$Br_3$ |
| 34. | 2,3,4,5,6-$Br_5$ |
| 35. | 2-I |
| 36. | 3-I |
| 37. | 4-I |
| 38. | 2,4-$I_2$ |
| 39. | 2-Cl, 3-F |
| 40. | 2-Cl, 4-F |
| 41. | 2-Cl, 5-F |
| 42. | 2-Cl, 6-F |
| 43. | 2-Cl, 3-Br |
| 44. | 2-Cl, 4-Br |
| 45. | 2-Cl, 5-Br |
| 46. | 2-Cl, 6-Br |
| 47. | 2-Br, 3-Cl |

TABLE A-continued

| No. | R$^x$ |
|---|---|
| 48. | 2-Br, 4-Cl |
| 49. | 2-Br, 5-Cl |
| 50. | 2-Br, 3-F |
| 51. | 2-Br, 4-F |
| 52. | 2-Br, 5-F |
| 53. | 2-Br, 6-F |
| 54. | 2-F, 3-Cl |
| 55. | 2-F, 4-Cl |
| 56. | 2-F, 5-Cl |
| 57. | 3-Cl, 4-F |
| 58. | 3-Cl, 5-F |
| 59. | 3-Cl, 4-Br |
| 60. | 3-Cl, 5-Br |
| 61. | 3-F, 4-Cl |
| 62. | 3-F, 4-Br |
| 63. | 3-Br, 4-Cl |
| 64. | 3-Br, 4-F |
| 65. | 2,6-Cl$_2$, 4-Br |
| 66. | 2-CH$_3$ |
| 67. | 3-CH$_3$ |
| 68. | 4-CH$_3$ |
| 69. | 2,3-(CH$_3$)$_2$ |
| 70. | 2,4-(CH$_3$)$_2$ |
| 71. | 2,5-(CH$_3$)$_2$ |
| 72. | 2,6-(CH$_3$)$_2$ |
| 73. | 3,4-(CH$_3$)$_2$ |
| 74. | 3,5-(CH$_3$)$_2$ |
| 75. | 2,3,5-(CH$_3$)$_3$ |
| 76. | 2,3,4-(CH$_3$)$_3$ |
| 77. | 2,3,6-(CH$_3$)$_3$ |
| 78. | 2,4,5-(CH$_3$)$_3$ |
| 79. | 2,4,6-(CH$_3$)$_3$ |
| 80. | 3,4,5-(CH$_3$)$_3$ |
| 81. | 2,3,4,6-(CH$_3$)$_4$ |
| 82. | 2,3,5,6-(CH$_3$)$_4$ |
| 83. | 2,3,4,5,6-(CH$_3$)$_5$ |
| 84. | 2-C$_2$H$_5$ |
| 85. | 3-C$_2$H$_5$ |
| 86. | 4-C$_2$H$_5$ |
| 87. | 2,4-(C$_2$H$_5$)$_5$ |
| 88. | 2,6-(C$_2$H$_5$)$_2$ |
| 89. | 3,5-(C$_2$H$_5$)$_2$ |
| 90. | 2,4,6-(C$_2$H$_5$)$_3$ |
| 91. | 2-n-C$_3$H$_7$ |
| 92. | 3-n-C$_3$H$_7$ |
| 93. | 4-n-C$_3$H$_7$ |
| 94. | 2-i-C$_3$H$_7$ |
| 95. | 3-i-C$_3$H$_7$ |
| 96. | 4-i-C$_3$H$_7$ |
| 97. | 2,4-(i-C$_3$H$_7$)$_2$ |
| 98. | 2,6-(i-C$_3$H$_7$)$_2$ |
| 99. | 3,5-(i-C$_3$H$_7$)$_2$ |
| 100. | 2-s-C$_4$H$_9$ |
| 101. | 3-s-C$_4$H$_9$ |
| 102. | 4-s-C$_4$H$_9$ |
| 103. | 2-t-C$_4$H$_9$ |
| 104. | 3-t-C$_4$H$_9$ |
| 105. | 4-t-C$_4$H$_9$ |
| 106. | 4-n-C$_9$H$_{19}$ |
| 107. | 2-CH$_3$, 4-t-C$_4$H$_9$ |
| 108. | 2-CH$_3$, 6-t-C$_4$H$_9$ |
| 109. | 2-CH$_3$, 4-i-C$_3$H$_7$ |
| 110. | 2-CH$_3$, 5-i-C$_3$H$_7$ |
| 111. | 3-CH$_3$, 4-i-C$_3$H$_7$ |
| 112. | 2-cyclo-C$_6$H$_{11}$ |
| 113. | 3-cyclo-C$_6$H$_{11}$ |
| 114. | 4-cyclo-C$_6$H$_{11}$ |
| 115. | 2-Cl, 4-C$_6$H$_5$ |
| 116. | 2-Br, 4-C$_6$H$_5$ |
| 117. | 2-OCH$_3$ |
| 118. | 3-OCH$_3$ |
| 119. | 4-OCH$_3$ |
| 120. | 2-OC$_2$H$_5$ |
| 121. | 3-O-C$_2$H$_5$ |
| 122. | 4-O-C$_2$H$_5$ |
| 123. | 2-O-n-C$_3$H$_7$ |
| 124. | 3-O-n-C$_3$H$_7$ |
| 125. | 4-O-n-C$_3$H$_7$ |
| 126. | 2-O-i-C$_3$H$_7$ |
| 127. | 3-O-i-C$_3$H$_7$ |
| 128. | 4-O-i-C$_3$H$_7$ |
| 129. | 2-O-n-C$_6$H$_{13}$ |
| 130. | 3-O-n-C$_6$H$_{13}$ |
| 131. | 4-O-n-C$_6$H$_{13}$ |
| 132. | 2-O-CH$_2$C$_6$H$_5$ |
| 133. | 3-O-CH$_2$C$_6$H$_5$ |
| 134. | 4-O-CH$_2$C$_6$H$_5$ |
| 135. | 2-O-(CH$_2$)3C$_6$H$_5$ |
| 136. | 4-O-(CH$_2$)3C$_6$H$_5$ |
| 137. | 2,3-(OCH$_3$)$_2$ |
| 138. | 2,4-(OCH$_3$)$_2$ |
| 139. | 2,5-(OCH$_3$)$_2$ |
| 140. | 2,6-(OCH$_3$)$_2$ |
| 141. | 3,4-(OCH$_3$)$_2$ |
| 142. | 3,5-(OCH$_3$)$_2$ |
| 143. | 2-O-t-C$_4$H$_9$ |
| 144. | 3-O-t-C$_4$H$_9$ |
| 145. | 4-O-t-C$_4$H$_9$ |
| 146. | 3-(3'-Cl-C$_6$H$_4$) |
| 147. | 4-(4'-CH$_3$-C$_6$H$_4$) |
| 148. | 2-O-C$_6$H$_5$ |
| 149. | 3-O-C$_6$H$_5$ |
| 150. | 4-O-C$_6$H$_5$ |
| 151. | 2-O-(2'-F-C$_6$H$_4$) |
| 152. | 3-O-(3'-Cl-C$_6$H$_4$) |
| 153. | 4-O-(4'-CH$_3$-C$_6$H$_4$) |
| 154. | 2,3,6-(CH$_3$)$_3$, 4-F |
| 155. | 2,3,6-(CH$_3$)$_3$, 4-Cl |
| 156. | 2,3,6-(CH$_3$)$_3$, 4-Br |
| 157. | 2,4-(CH$_3$)$_2$, 6-F |
| 158. | 2,4-(CH$_3$)$_2$, 6-Cl |
| 159. | 2,4-(CH$_3$)$_2$, 6-Br |
| 160. | 2-i-C$_3$H$_7$, 4-Cl, 5-CH$_3$ |
| 161. | 2-Cl, 4-NO$_2$ |
| 162. | 2-NO$_2$, 4-Cl |
| 163. | 2-OCH$_3$, 5-NO$_2$ |
| 164. | 2,4-Cl$_2$, 5-NO$_2$ |
| 165. | 2,4-Cl$_2$, 6-NO$_2$ |
| 166. | 2,6-Cl$_2$, 4-NO$_2$ |
| 167. | 2,6-BR$_2$, 4-NO$_2$ |
| 168. | 2,6-I$_2$, 4-NO$_2$ |
| 169. | 2-CH$_3$, 5-i-C$_3$H$_7$, 4-Cl |
| 170. | 2-CO$_2$CH$_3$ |
| 171. | 3-CO$_2$CH$_3$ |
| 172. | 4-CO$_2$CH$_3$ |
| 173. | 2-CH$_2$-OCH$_3$ |
| 174. | 3-CH$_2$-OCH$_3$ |
| 175. | 4-CH$_2$-OCH$_3$ |
| 176. | 2-Me-4-CH$_3$-CH(CH$_3$)-CO |
| 177. | 2-CH$_3$-4-(CH$_3$-C=NOCH$_3$) |
| 178. | 2-CH$_3$-4-(CH$_3$-C=NOC$_2$H$_5$) |
| 179. | 2-CH$_3$-4-(CH$_3$-C=NO-n-C$_3$H$_7$) |
| 180. | 2-CH$_3$-4-(CH$_3$-C=NO-i-C$_3$H$_7$) |
| 181. | 2,5-(CH$_3$)$_2$-4-(CH$_3$-C=NOCH$_3$) |
| 182. | 2,5-(CH$_3$)$_2$-4-(CH$_3$-C=NOC$_2$H$_5$) |
| 183. | 2,5-(CH$_3$)$_2$-4-(CH$_3$-C=NO-n-C$_3$H$_7$) |
| 184. | 2,5-(CH$_3$)$_2$-4-(CH$_3$-C=NO-i-C$_3$H$_7$) |
| 185. | 2-C$_6$H$_5$ |
| 186. | 3-C$_6$H$_5$ |
| 187. | 4-C$_6$H$_5$ |
| 188. | 2-(2'-F-C$_6$H$_4$) |
| 189. | 2-CH$_3$, 5-Br |
| 190. | 2-CH$_3$, 6-Br |
| 191. | 2-Cl, 3-CH$_3$ |
| 192. | 2-Cl, 4-CH$_3$ |
| 193. | 2-Cl, 5-CH$_3$ |
| 194. | 2-F, 3-CH$_3$ |
| 195. | 2-F, 4-CH$_3$ |
| 196. | 2-F, 5-CH$_3$ |
| 197. | 2-Br, 3-CH$_3$ |
| 198. | 2-Br, 4-CH$_3$ |
| 199. | 2-Br, 5-CH$_3$ |
| 200. | 3-CH$_3$, 4-Cl |
| 201. | 3-CH$_3$, 5-Cl |

TABLE A-continued

| No. | R$^x$ |
|---|---|
| 202. | 3-CH$_3$, 4-F |
| 203. | 3-CH$_3$, 5-F |
| 204. | 3-CH$_3$, 4-Br |
| 205. | 3-CH$_3$, 5-Br |
| 206. | 3-F, 4-CH$_3$ |
| 207. | 3-Cl, 4-CH$_3$ |
| 208. | 3-Br, 4-CH$_3$ |
| 209. | 2-Cl, 4,5-(CH$_3$)$_2$ |
| 210. | 2-Br, 4,5-(CH$_3$)$_2$ |
| 211. | 2-Cl, 3,5-(CH$_3$)$_2$ |
| 212. | 2-Br, 3,5-(CH$_3$)$_2$ |
| 213. | 2,6-Cl$_2$, 4-CH$_3$ |
| 214. | 2,6-F$_2$, 4-CH$_3$ |
| 215. | 2,6-Br$_2$, 4-CH$_3$ |
| 216. | 2,4-Br$_2$, 6-CH$_3$ |
| 217. | 2,4-F$_2$, 6-CH$_3$ |
| 218. | 2,4-BR$_2$, 6-CH$_3$ |
| 219. | 2,6-(CH$_3$)$_2$, 4-F |
| 220. | 2,6-(CH$_3$)$_2$, 4-Cl |
| 221. | 2,6-(CH$_3$)$_2$, 4-Br |
| 222. | 3,5-(CH$_3$)$_2$, 4-F |
| 223. | 3,5-(CH$_3$)$_2$, 4-Cl |
| 224. | 3,5-(CH$_3$)$_2$, 4-Br |
| 225. | 2-CF$_3$ |
| 226. | 3-CF$_3$ |
| 227. | 4-CF$_3$ |
| 228. | 2-OCF$_3$ |
| 229. | 3-OCF$_3$ |
| 230. | 4-OCF$_3$ |
| 231. | 3-OCH$_2$CHF$_2$ |
| 232. | 2-NO$_2$ |
| 233. | 3-NO$_2$ |
| 234. | 4-NO$_2$ |
| 235. | 2-CN |
| 236. | 3-CN |
| 237. | 4-CN |
| 238. | 2-CH$_3$, 3-Cl |
| 239. | 2-CH$_3$, 4-Cl |
| 240. | 2-CH$_3$, 5-Cl |
| 241. | 2-CH$_3$, 6-Cl |
| 242. | 2-CH$_3$, 3-F |
| 243. | 2-CH$_3$, 4-F |
| 244. | 2-CH$_3$, 5-F |
| 245. | 2-CH$_3$, 6-F |
| 246. | 2-CH$_3$, 3-Br |
| 247. | 2-CH$_3$, 4-Br |
| 248. | 2,5-F$_2$ |
| 249. | 2,6-F$_2$ |
| 250. | 3,4-F$_2$ |
| 251. | 3,5-F$_2$ |

TABLE B

| No. | R$^2$ | R$^3$ | R$^4$ |
|---|---|---|---|
| 1 | H | CH$_3$ | phenyl |
| 2 | C$_2$H$_5$ | CH$_3$ | phenyl |
| 3 | n-C$_3$H$_7$ | CH$_3$ | phenyl |
| 4 | i-C$_3$H$_7$ | CH$_3$ | phenyl |
| 5 | cyclopropyl | CH$_3$ | phenyl |
| 6 | pyridinyl-2 | CH$_3$ | phenyl |
| 7 | pyridinyl-3 | CH$_3$ | phenyl |
| 8 | pyridinyl-4 | CH$_3$ | phenyl |
| 9 | 5-CH$_3$-isoxazolyl-3 | CH$_3$ | phenyl |
| 10 | phenyl | CH$_3$ | phenyl |
| 11 | CH$_3$ | H | phenyl |
| 12 | CH$_3$ | C$_2$H$_5$ | phenyl |
| 13 | CH$_3$ | n-C$_3$H$_7$ | phenyl |
| 14 | CH$_3$ | i-C$_3$H$_7$ | phenyl |
| 15 | CH$_3$ | cyclopropyl | phenyl |
| 16 | CH$_3$ | pyridinyl-2 | phenyl |
| 17 | CH$_3$ | pyridinyl-3 | phenyl |
| 18 | CH$_3$ | pyridinyl-4 | phenyl |
| 19 | CH$_3$ | 3-CH$_3$-isoxazolyl-5 | phenyl |
| 20 | CH$_3$ | phenyl | phenyl |
| 21 | H | CH$_3$ | CH$_3$ |
| 22 | CH$_3$ | CH$_3$ | CH$_3$ |
| 23 | C$_2$H$_5$ | CH$_3$ | CH$_3$ |
| 24 | n-C$_3$H$_7$ | CH$_3$ | CH$_3$ |
| 25 | i-C$_3$H$_7$ | CH$_3$ | CH$_3$ |
| 26 | cyclopropyl | CH$_3$ | CH$_3$ |
| 27 | pyridinyl-2 | CH$_3$ | CH$_3$ |
| 28 | pyridinyl-3 | CH$_3$ | CH$_3$ |
| 29 | pyridinyl-4 | CH$_3$ | CH$_3$ |
| 30 | 5-CH$_3$-isoxazolyl-3 | CH$_3$ | CH$_3$ |
| 31 | phenyl | CH$_3$ | CH$_3$ |
| 32 | CH$_3$ | H | CH$_3$ |
| 33 | CH$_3$ | C$_2$H$_5$ | CH$_3$ |
| 34 | CH$_3$ | n-C$_3$H$_7$ | CH$_3$ |
| 35 | CH$_3$ | i-C$_3$H$_7$ | CH$_3$ |
| 36 | CH$_3$ | cyclopropyl | CH$_3$ |
| 37 | CH$_3$ | pyridinyl-2 | CH$_3$ |
| 38 | CH$_3$ | pyridinyl-3 | CH$_3$ |
| 39 | CH$_3$ | pyridinyl-4 | CH$_3$ |
| 40 | CH$_3$ | 3-CH$_3$-isoxazolyl-5 | CH$_3$ |
| 41 | CH$_3$ | phenyl | CH$_3$ |

TABLE C

| No. | R$^2$ | R$^3$ | R$^d$ | R$^e$ |
|---|---|---|---|---|
| 1 | H | CH$_3$ | CH$_3$ | CH$_3$ |
| 2 | CH$_3$ | CH$_3$ | CH$_3$ | CH$_3$ |
| 3 | C$_2$H$_5$ | CH$_3$ | CH$_3$ | CH$_3$ |
| 4 | n-C$_3$H$_7$ | CH$_3$ | CH$_3$ | CH$_3$ |
| 5 | i-C$_3$H$_7$ | CH$_3$ | CH$_3$ | CH$_3$ |
| 6 | cyclopropyl | CH$_3$ | CH$_3$ | CH$_3$ |
| 7 | pyridinyl-2 | CH$_3$ | CH$_3$ | CH$_3$ |
| 8 | pyridinyl-3 | CH$_3$ | CH$_3$ | CH$_3$ |
| 9 | pyridinyl-4 | CH$_3$ | CH$_3$ | CH$_3$ |
| 10 | 5-CH$_3$-isoxazolyl-3 | CH$_3$ | CH$_3$ | CH$_3$ |
| 11 | phenyl | CH$_3$ | CH$_3$ | CH$_3$ |
| 12 | CH$_3$ | H | CH$_3$ | CH$_3$ |
| 13 | CH$_3$ | C$_2$H$_5$ | CH$_3$ | CH$_3$ |
| 14 | CH$_3$ | n-C$_3$H$_7$ | CH$_3$ | CH$_3$ |
| 15 | CH$_3$ | i-C$_3$H$_7$ | CH$_3$ | CH$_3$ |
| 16 | CH$_3$ | cyclopropyl | CH$_3$ | CH$_3$ |
| 17 | CH$_3$ | pyridinyl-2 | CH$_3$ | CH$_3$ |
| 18 | CH$_3$ | pyridinyl-3 | CH$_3$ | CH$_3$ |
| 19 | CH$_3$ | pyridinyl-4 | CH$_3$ | CH$_3$ |
| 20 | CH$_3$ | 3-CH$_3$-isoxazolyl-5 | CH$_3$ | CH$_3$ |
| 21 | CH$_3$ | CH$_3$ | H | CH$_3$ |
| 22 | CH$_3$ | CH$_3$ | C$_2$H$_5$ | CH$_3$ |
| 23 | CH$_3$ | CH$_3$ | n-C$_3$H$_7$ | CH$_3$ |
| 24 | CH$_3$ | CH$_3$ | i-C$_3$H$_7$ | CH$_3$ |
| 25 | CH$_3$ | CH$_3$ | cyclopropyl | CH$_3$ |
| 26 | CH$_3$ | CH$_3$ | pyridinyl-2 | CH$_3$ |
| 27 | CH$_3$ | CH$_3$ | pyridinyl-3 | CH$_3$ |
| 28 | CH$_3$ | CH$_3$ | pyridinyl-4 | CH$_3$ |
| 29 | CH$_3$ | CH$_3$ | 3-CH$_3$-isoxazolyl-5 | CH$_3$ |
| 30 | CH$_3$ | CH$_3$ | CH$_3$ | C$_2$H$_5$ |
| 31 | CH$_3$ | CH$_3$ | CH$_3$ | n-C$_3$H$_7$ |
| 32 | CH$_3$ | CH$_3$ | CH$_3$ | i-C$_3$-H$_7$ |
| 33 | CH$_3$ | CH$_3$ | CH$_3$ | t-C$_4$H$_9$ |
| 34 | CH$_3$ | CH$_3$ | CH$_3$ | benzyl |
| 35 | CH$_3$ | CH$_3$ | CH$_3$ | propargyl |
| 36 | CH$_3$ | CH$_3$ | CH$_3$ | bromopropargyl |
| 37 | CH$_3$ | CH$_3$ | CH$_3$ | iodopropargyl |
| 38 | CH$_3$ | CH$_3$ | CH$_3$ | allyl |
| 39 | CH$_3$ | CH$_3$ | CH$_3$ | trans-chloroallyl |
| 40 | CH$_3$ | CH$_3$ | CH$_3$ | CH$_3$-O-CH$_2$-CH$_2$ |

TABLE D physical data of some selected compounds

| No. | formula | R² | R³ | R⁴ | R^d | R^e | m.p. [° C.] NMR [ppm] or IR [cm⁻¹] |
|---|---|---|---|---|---|---|---|
| 1 | Ia.1.1 | CH₃ | CH₃ | — | CH₃ | CH₃ | 104–106 |
| 2 | Ib.1.1 | CH₃ | CH₃ | — | CH₃ | CH₃ | 114–116 |
| 3 | Ia.1.1 | CH₃ | CH₃ | — | phenyl | CH₃ | 117–118 |
| 4 | Ib.1.1 | CH₃ | CH₃ | — | phenyl | CH₃ | 139–140 |
| 5 | Ia.1.1 | phenyl | CH₃ | — | CH₃ | CH₃ | 100–101 |
| 6 | Ia.1.3 | CH₃ | CH₃ | — | CH₃ | CH₃ | 76–79 |
| 7 | Ia.1.2 | CH₃ | CH₃ | — | CH₃ | CH₃ | 57–58 |
| 8 | Ib.1.1 | phenyl | CH₃ | — | CH₃ | CH₃ | 64–67 |
| 9 | Ia.1 | CH₃ | CH₃ | phenyl | — | — | 72–73 |
| 10 | Ib.1 | CH₃ | CH₃ | phenyl | — | — | 85–89 |

The compounds I are useful as fungicides.

The compounds I are distinguished by an outstanding activity against a broad spectrum of phytopathogenic fungi, in particular from the classes of the Ascomycetes, Phycomycetes and Basidiomycetes. Some of them act systemically and can be employed as foliar- and soil-acting fungicides.

They are especially important for controlling a large number of fungi in a variety of crop plants such as wheat, rye, barley, oats, rice, maize, grass, cotton, soya, coffee, sugar cane, grapevine, fruit species, ornamentals and vegetable species such as cucumbers, beans and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat, barley, *Pyricularia oryzae* in rice, Phytophthora infestans in potatoes and tomatoes, Fusarium and Verticillium species in various plants, *Plasmopara viticola* in grapevines, Alternaria species in vegetables and fruit and Pseudoperonospora species in hops and cucurbits.

The compounds I are used by treating the fungi, or the plants, seeds, materials or the soil to be protected against fungal infection, with a fungicidally effective amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform distribution of the compounds according to the invention. The formulations are prepared in a known manner, for example by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzene, paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants, such as lignosulfite waste liquors and methylcellulose.

In general, the fungicidal compositions comprise from 0.1 to 95, preferably from 0.5 to 90, % by weight of active ingredient.

Depending on the nature of the desired effect, the rates of application are from 0.01 to 2.0 kg of active ingredient per ha.

For seed treatment, amounts of active ingredient of from 0.001 to 0.1 g, preferably 0.01 to 0.05 g, are generally required per kilogram of seed.

In their use form as fungicides, the compositions according to the invention can also be present together with other active ingredients, the [sic] eg. with herbicides, insecticides, growth regulators, fungicides or else fertilizers.

A mixture with fungicides frequently results in a widening of the fungicidal spectrum of action.

The following list of fungicides together with which the compounds according to the invention can be used are intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

Nitro derivatives such as dinitro(1-methylheptyl)phenyl crotonate, 2-sec-butyl-4,6-dinitrophenyl-3,3-dimethyl acrylate, 2-sec-butyl-4,6-dinitrophenyl isopropyl carbonate, diisopropyl 5-nitroisophthalate;

heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)-phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2, 2-tetrachloroethylthio)tetrahydrophthalimide, N-trichloromethylthiotetrahydrophthalimide, N-trichloromethylthiophthalimide, N-(4,6-dimethylpyrimidine-2-yl)aniline, N-(4-methyl-6-(1-propynyl)-pyrimidine-2-yl)aniline, N-(4-methyl-6-cyclopropyl-pyrimidine-2-yl)aniline, methyl (E)-methoximino[α-(2-methyl-phenoxy)-o-tolyl]acetate, N-methyl-(E)-methoximino[α-2,5-dimethylphenoxyl-o-tolyl]acetamide, methyl (E)-2-[2-(6-(2-cyanophenoxy) pyrimidine-4-yloxy)phenyl]-3-methoxyacrylate, 2,6-dimethyl-N-cyclododecylmorpholine and its salts, N-[3-(p-tert-butylphenyl)-2-methylpropyl)-cis-2,6-dimethylmorpholine, N-[3-(p-tert-butylphenyl)-2-methylpropyl)piperidine, 1-[2-(2,4-dichlorophenyl)-4-ethyl-1,3-dioxolan-2-ylethyl]-1H-1,2,4-triazole, 1-[2-(2, 4-dichlorophenyl)-4-n-propyl-1,3-dioxolan-2-ylethyl)-1H-1,2,4-triazole, N-(n-propyl)-N-(2,4,6-trichlorophenoxyethyl)-N'-imidazolyl urea, 1-(4- chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido)benzene, 1-2-bis(3-methoxycarbonyl-2-thioureido)benzene, N-dichlorofluoromethylthio-N',N'-dimethyl-N-phenylsulfuric acid diamide, 5-ethoxy-3-trichloromethyl-1,2,4-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-[2,2,2-trichloroethyl-1-(4-morpholinyl)]formamide, piperazine-1,4-diylbis-(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, DL-methyl N-(2,6-dimethylphenyl)-N-furoyl(2)-alaninate, DL-methyl N-(2,6-dimethylphenyl)-N-(2'-methoxyacetyl)alaninate, N-(2,6-dimethylphenyl)-N-chloroacetyl-D,L-2-aminobutyrolactone, DL-methyl N-(2,6-dimethylphenyl)-N-(phenylacetyl)alaninate, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorophenyl)-1-isopropylcarbamoyl-hydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethylphenyl)-5-trifluoro-methyl-3-chloro-2-aminopyridine, 1-((bis(4-fluorophenyl)methylsilyl)methyl)-1H-1,2,4-triazole, 4-(2,2-difluoro-1,3-benzodioxol-4-yl)pyrrole-3-carbonitrile, (2RS,3SR(-1[3-(2-chlorophenyl)-2-(4-fluorophenyl)oxiran-2-ylmethyl]-1H-1,2,4-triazole.

The compounds of the formula I are furthermore useful for controlling pests from the classes of the insects, arachnids and nematodes. They can be employed as pesticides in crop protection, and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticti-Kalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius Kalifornicus* [sic], *Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hynenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus asKalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Kalotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cyst nematodes, eg. *Globodera rostochiensis, Heterodera avenae, Heterodera glycines, Heterodera schachtii, Heterodera trifolii,* stem eel worms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be applied as such, in the form of their formulations or the use forms prepared therefrom, eg. in the form of directly sprayable solutions, powders, suspensions or dispersions, emulsions, oil dispersions, pastes, dusts, mateirals for spreading, and granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can vary within substantial ranges.

In general, they are from 0.0001 to 10%, preferably from 0.01 to 1%.

The active ingredients can also be employed very successfully in the ultra-low-volume method (ULV), it being possible to apply formulations comprising more than 95% by weight of active ingredient, or even the active ingredient without additives.

Under field conditions, the rate of active ingredient to be applied for controlling pests is from 0.1 to 2.0, preferably 0.2 to 1.0, kg/ha.

Substances which are suitable for preparing directly sprayable solutions, emulsions, pastes or oil dispersions are mineral oil fractions of medium to high boiling point, such as kerosene or diesel oil, furthermore coal tar oils, and oils of vegetable or animal origin, aliphatic, cyclic or aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, adhesive, dispersant or emulsifier. Alternatively, it is possible to prepare concentrates from active ingredient, wetting agent, adhesive, dispersant or emulsifier and, if desired, solvent or oil, which are suitable for dilution with water.

Suitable surfactants are alkali, alkaline earth and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali and alkaline earth metal salts, salts of sulfated fatty alcohol glycol ether, condensates of sulfonated naphthalene and naphthelane derivatives with formaldehyde, condensates of naphthalene or of the naphtalenesulfonic acid with phenol and formaldehyde, polyoxyethylene octylphenol ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Powders, materials for spreading and dusts can be prepared by mixing or concomitantly grinding the active ingredients with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

Examples of formulations are

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil, which have been sprayed onto the surface of this silica gel. This gives a preparation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, and this gives a solution which is useful for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients onto solid carriers. Examples of solid carriers are mineral earths such as silica gel, silicas, silica gels, silicates, talc, kaolin, attaclay, limestone, lime, chalk, bole, loess, clay, dolomite, diatomacious earth, calcium sulfate, magnesium sulfate, magnesium oxide, ground synthetic materials, fertilizers, eg. ammonium sulfate, ammonium phosphate, ammonium nitrate, ureas and products of vegetable origin such as cereal meal, tree bark meal, wood meal and nutshell meal, cellulose powders and other solid carriers.

Various types of oils, or herbicides, fungicides, other pesticides, and bactericides, can be added to the active ingredients, if appropriate also just before use (tank mix). These agents can be admixed with the agents according to the invention in a weight ratio of 1:10 to 10:1.

SYNTHESIS EXAMPLES

The protocols given in the synthesis examples which follow were also used for obtaining other compounds I by altering the starting compounds as required. The resulting compounds together with physical data are listed in the tables which follow.

1. Preparation of

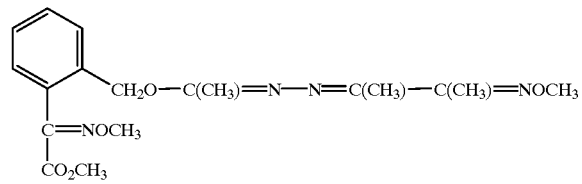

I.001 a. Diacetyl O-methyloxime N-acetylhydrazone

A mixture of 6.0 g (52 mmol) of diacetyl O-methyloxime, 3.9 g (52 mmol) of acetylhydrazine and 3 drops of concentrated hydrochloric acid in 50 ml of methanol was stirred overnight (approximately 12 hours) at room temperature (approximately 20° C.). The product which crystallized out was isolated. The mother liquor was concentrated, small quantities of product crystallizing out. In total, 4.0 g (45%) of the title compound was obtained.

$^1$H NMR, $d_6$-DMSO, δ in ppm): 1.95 (s, 3H, CH$_3$), 2.00 (s, 3H, CH$_3$), 2.20 (s, 3H, CH$_3$), 3.90 (s, 3H, OCH$_3$), 10.60 (s, broad, 1H, NH)

b. Title compound

A mixture of 2.5 g (15 mmol) of the product of a) and 20 ml of dimethylformamide was first treated with 0.45 g (19 mmol) of sodium hydride and then stirred at room temperature until the evolution of gas had ceased. The resulting mixture was then treated with 4.2 g (15 mmol) of methyl α-keto-2-bromomethylphenylacetate trans-O-methyloxime (according to EP-A 254 426). After approximately 12 hours at room temperature, the resulting mixture was diluted with water. The title compound was isolated by extraction using tert-butyl methyl ether. The crude product obtained after washing, drying and concentrating the ether phase was purified by column chromatography (silica gel, cyclohexane/ethyl acetate). This gave 1.6 g (28%) of the title compound in the form of colorless crystals (m.p.: 105° C.)

$^1$H NMR, $d_6$-DMSO, δ in ppm): 2.05 (s, 3H, CH$_3$), 2.10 (2s, in each case 3H, 2×CH$_3$), 3.85 (s, 3H, OCH$_3$), 4.00 (s, 3H, OCH$_3$), 4.05 (s, 3H, OCH$_3$), 5.20 (s, 2H, OCH$_2$), 7.20 (d, broad, 1H, phenyl), 7.35–7.55 (m, 3H, phenyl)

2. Preparation of

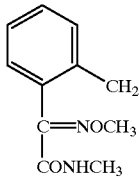

I.002

A mixture of 1.0 g (2.6 mmol) of the compound of Example 1b) and 20 ml of 40% strength aqueous methylamine solution is stirred for 3 hours at room temperature and subsequently diluted with water. The title compound was isolated by extraction with methylene chloride. The crude product obtained after washing, drying and concentrating the organic phase was purified by digestion with hexane. This gave 0.55 g (55%) of the title compound in the form of colorless crystals (m.p.: 115° C.)

$^1$H NMR (CDCl$_3$, δ in ppm): 2.05 (s, 3H, CH$_3$), 2.10 (2s, in each case 3H, 2×CH$_3$), 2.90 (d, 3H, NCH$_3$), 3.95 (s, 3H, OCH$_3$), 4.00 (s, 3H, OCH$_3$), 5.10 (s, 2H, OCH$_2$), 6.80 (s, very broad, 1H, NH), 7.20 (m, 1H, phenyl), 7.40 (m, 2H, phenyl) 7.50 (m, 1H, phenyl)

EXAMPLES

Activity Against Harmful Fungi

The fungicidal activity of the compounds of the formula I was demonstrated by the following experiments:

The active ingredients were prepared as a 10% emulsion in a mixture of 70% by weight of cyclohexanone, 20% by weight of Nekanil® LN (Lutensol® AP6, wetting agent with emulsifying and dispersant action based on ethoxylated alkylphenols) and 10% by weight of Emulphor® EL (Emulan® EL, emulsifier based on ethoxylated fatty alcohols) and diluted with water to give the desired concentration.

A. Activity Against *Plasmopara viticola* (Downy Mildew of Grapevines)

Grapevines in pots (cultivar: "Müller Thurgau") were sprayed to drip point with the preparation of the active ingredient. After 8 days, the plants were sprayed with a zoospore suspension of the fungus *Plasmopara viticola* and kept for 5 days at 20–30° C. and high atmospheric humidity. Prior to assessment, the plants were returned for 16 hours to high atmospheric humidity. Evaluation was carried out visually.

In this test, a disease level of 0 to 15% was observed on the plants which had been treated with 250 ppm of the compounds Nos 1, 2, 3, 6, 7, 8, 9 and 10 of Table D according to the invention, while the disease level of the untreated plants was 70%.

B. Activity Against *Pyricularia oryzae* (Rice Blast Disease)

Rice seedlings (cultivar: "Nai Tong 67") were sprayed to drip point with the preparation of the active ingredient. After 24 hours, the plants were sprayed with an aqueous spore suspension of the fungus *Pyricularia pryzae* [sic] and kept for 6 days at 22–24° C. and a relative atmospheric humidity of 95–99%. Evaluation was carried out visually.

In this test, a disease level of 0 to 15% was observed on the plants which had been treated with 250 ppm of the compounds Nos 2, 3, 4, 6, 7, 9 and 10 of Table D according to the invention, while the disease level of the untreated plants was 90%.

EXAMPLES

Activity Against Animal Pests

The activity of the compounds of the general formula I against animal pests was demonstrated by the following experiments:

The active ingredients were formulated
a) as a 0.1% strength solution in acetone or
b) as a 10% emulsion in a mixture of 70% by weight of cyclohexanone, 20% by weight of Nekanil® LN (Lutensol® AP6, wetting agent with emulsifying and dispersant action based on ethoxylated alkylphenols) and 10% by weight of Emulphor® EL (Emulan® EL, emulsifier based on ethoxylated fatty alcohols)
and diluted to give the desired concentration, using acetone in the case of a) and water in the case of b).

After the experiments had ended, the lowest concentration was determined where in each case an 80 to 100% inhibition or mortality was caused by the compounds in comparison with untreated control experiments (critical concentration or minimal concentration).

A) Activity Against *Nephotettix cincticeps* (Green Rice Leafhopper), Contact Experiment Circular filters (ø9 cm) were treated with 1 cm$^3$ of the aqueous preparation of the active ingredient and placed into a plastic Petri dish provided with ridges (ø94 mm). 5 adult rice leafhoppers were subsequently introduced, and the Petri dish was sealed.

If no formulated substance is present, the experiment is carried out with a solution of the active ingredient in acetone, and glass Petri dishes are used (ø10 cm). After the acetone has evaporated, the filter is moistened with 1 cm$^3$ of water.

The mortality was assessed after 24 hours.

In this test, a critical concentration of 0.2 mg was determined for compound 6 of Table D.

B) Activity Against *Aphis fabae* (Black Bean Aphid), Contact Action, Spray Test Young bean plants (*Vicia faba*) in the 4-leaf stage which were populated with a large colony of black bean aphid were treated with the aqueous preparation of the test substance. To this end, the plants were guided onto the revolving plate of the spray cabin via a rail and sprayed from all sides with 3 nozzles pointing in different directions, applying 30 cm$^3$ of solution of the active ingredient.

The test was evaluated after 24 hours.

At an active ingredient concentration of 400 ppm, compound 6 of Table D caused a mortality of 80%.

C) Activity Against *Tetranychus urticae* (Greenhouse Red Spider Mite), Contact Action, Spray Test In the spray cabin, dwarf beans in pots with one fully formed pair of leaves were sprayed to drip point with the aqueous solution of the active ingredient. To this end, the plants were guided onto the revolving plate of the spray cabin via a rail and sprayed from all sides with 3 nozzles pointing in different directions, applying 30 cm$^3$ of solution of the active ingredient. The spraying procedure took approximately 20 seconds. The plants were severely infested with mites, and a large number of eggs had been deposited.

The activity was assessed after 5 days using a stereomicroscope. It was established whether all stages had been affected to the same extent. During this time, the plants stayed under normal greenhouse conditions.

In this test, compound 6 of Table D showed a critical concentration of 20 ppm.

We claim:
1. A phenylacetic acid derivative of the formula I

$$\text{R}_m\text{—}\underset{\underset{\text{COYR}^1}{\overset{\|}{\text{C=X}}}}{\text{C}_6\text{H}_4}\text{—CH}_2\text{O—CR}^2\text{=N—N=CR}^3\text{R}^4 \quad \text{I}$$

where the substituents and the index have the following meanings:

X is $NOCH_3$, $CHOCH_3$ and $CHCH_3$;

Y is oxygen or $NR^a$;

$R^a$ is hydrogen or $C_1$–$C_4$-alkyl;

R is cyano, nitro, trifluoromethyl, halogen, $C_1$–$C_4$-alkyl and $C_1$–$C_4$-alkoxy;

m is 0, 1 or 2, it being possible for the radicals R to be different if m is 2;

$R^1$ is hydrogen or $C_1$–$C_6$-alkyl;

$R^2$ and $R^3$ independently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N—$C_3$–$C_6$-cycloalkenyl-N—$C_1$–$C_6$-alkylamino, heterocyclyl, heterocyclyloxy, heterocyclylthio, heterocyclylamino, N-heterocyclyl-N—$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—$D_n$—$R^g$;

A is oxygen, sulfur or nitrogen, the nitrogen having attached to it hydrogen or $C_1$–$C_6$-alkyl;

D is, oxygen or $NR^h$;

n is 0 or 1;

$R^b$, $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^4$ is one of the groups mentioned under $R^2$ or a group $CR^d$=$NOR^e$;

$R^d$ is one of the groups mentioned under $R^2$;

$R^e$ is hydrogen,
$C_1$–$C_{10}$-alkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or C(=NOR$^b$)—A$_n$—R$^c$;

$C_3$–$C_6$-cycloalkyl, aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, C(=NOR$^b$)—A$_n$—R$^c$ or NR$^f$—CO—D$_n$—R$^g$;

or a salt thereof.

2. A compound of the formula I as claimed in claim 1, where X is NOCH$_3$, CHOCH$_3$ or CHCH$_3$ and Y is oxygen.

3. A compound of the formula I as claimed in claim 1 where X is NOCH$_3$ and Y is NR$^a$.

4. A compound of the formula I as claimed in claim 1 where m is 0.

5. A compound of the formula I as claimed in claim 1 where R$^1$ is methyl.

6. A process for the preparation of a compound I as claimed in claim 1 where R$^2$ is other than halogen, which comprises reacting a benzyl derivative of the formula II

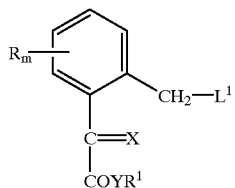

where L$^1$ is a nucleophilically exchangeable leaving group with a carbonylhydrazide of the formula III

wherein Rm, X, Y and R$^1$ to R$^4$ are defined as in claim 1.

7. A process for the preparation of a compound I as claimed in claim 1 where Y is NR$^a$, which comprises reacting the corresponding phenylacetic ester of the formula Ia

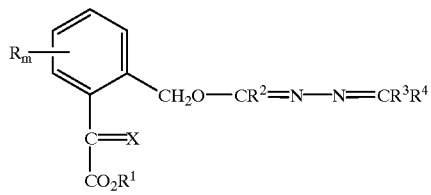

with an amine of the formula IV

wherein Rm, X and R$^1$ to R$^4$ are defined as in claim 1.

8. A composition which is useful for controlling pests or harmful fungi, comprising a solid or liquid carrier and a compound of the general formula I as claimed in claim 1.

9. A method of controlling harmful fungi, which comprises treating the fungi, or the materials, plants, soil or seeds to be protected against fungal infection, with an effective amount of a compound of the general formula I as claimed in claim 1.

10. A method of controlling pests, which comprises treating the pests, or the materials, plants, soil or seeds to be protected against them, with an effective amount of a compound of the general formula I as claimed in claim 1.

* * * * *